US00PP22373P2

(12) United States Plant Patent
Goemans

(10) Patent No.: US PP22,373 P2
(45) Date of Patent: Dec. 20, 2011

(54) ***ALSTROEMERIA* PLANT NAMED 'GINA'**

(50) Latin Name: *Alstroemeria hybrida*
Varietal Denomination: Gina

(75) Inventor: Francis Cornelius Goemans, Chichester (GB)

(73) Assignee: Wülfinghoff Alstroemeria B.V., Rijswijk (NL)

( * ) Notice: Subject to any disclaimer, the term of this patent is extended or adjusted under 35 U.S.C. 154(b) by 0 days.

(21) Appl. No.: 12/806,247

(22) Filed: Aug. 7, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — Susan McCormick Ewoldt
(74) *Attorney, Agent, or Firm* — C. A. Whealy

(57) ABSTRACT

A new and distinct cultivar of *Alstroemeria* plant named 'Gina', characterized by its compact and mounding plant habit; sturdy and strong plants; vigorous growth habit; large red purple and yellow-colored flowers; and good garden performance.

2 Drawing Sheets

Botanical designation: *Alstroemeria hybrida.*
Cultivar denomination: 'GINA'.

BACKGROUND OF THE INVENTION

The present invention relates to a new and distinct cultivar of *Alstroemeria* plant, botanically known as *Alstroemeria hybrida,* grown typically as a potted garden *Alstroemeria,* and hereinafter referred to by the name 'Gina'.

The new *Alstroemeria* plant is a product of a planned breeding program conducted by the Inventor in Chichester, England. The objective of the breeding program is to create new compact potted garden *Alstroemeria* cultivars that have attractive foliage and flower coloration.

The new *Alstroemeria* plant originated from a cross-pollination made by the Inventor in Chichester, England in June, 2004, of a proprietary selection of *Alstroemeria hybrida* identified as code number T39, not patented, as the female, or seed, parent with a proprietary *Alstroemeria hybrida* selection identified as code number 1205/35, not patented, as the male, or pollen, parent. The new *Alstroemeria* plant was discovered and selected by the Inventor as a flowering plant from within the progeny of the stated cross-pollination in a controlled greenhouse environment in Chichester, England in May, 2006.

Asexual reproduction of the new *Alstroemeria* plant by tissue culture in a controlled greenhouse environment in Chichester, England since October, 2008, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Gina'. These characteristics in combination distinguish 'Gina' as a new and distinct cultivar of *Alstroemeria* plant:

1. Compact and mounding plant habit.
2. Sturdy and strong plants.
3. Vigorous growth habit.
4. Large red purple and yellow-colored flowers.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are more compact than plants of female parent selection.
2. Plants of the new *Alstroemeria* and female parent selection differ in flower color as plants of female parent selection have dark pink-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* are more compact than plants of the male parent selection.
2. Plants of the new *Alstroemeria* and the male parent selection differ in flower color as plants of the male parent selection have pale yellow-colored flowers.

Plants of the new *Alstroemeria* can be compared to plants of the *Alstroemeria hybrida* 'Davina', disclosed in U.S. Plant Pat. No. 20,703. In side-by-side comparisons conducted in Chichester, England, plants of the new *Alstroemeria* differed from plants of 'Davina' in the following characteristics:

1. Plants of the new *Alstroemeria* were larger than plants of 'Davina'.
2. Plants of the new *Alstroemeria* had shorter flowers than plants of 'Davina'.
3. Plants of the new *Alstroemeria* and 'Davina' differed in flower color as plants of 'Davina' had salmon pink and yellow-colored flowers.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet comprises a side perspective view of a typical flowering plant of 'Gina' grown in a container.

The photograph on the second sheet is a close-up view of a typical flower of 'Gina'.

DETAILED BOTANICAL DESCRIPTION

The aforementioned photographs and following observations and measurements describe plants of the new *Alstroemeria* grown during the summer in 21-cm containers in a glass-covered greenhouse in Chichester, England and under typical *Alstroemeria* production conditions. During the production of the plants, day temperatures averaged 20° C. and night temperatures averaged 14° C. Plants were six months old when the photographs and description were taken. Color references are made to The Royal Horticultural Society Colour Chart, 2001 Edition, except where general terms of ordinary dictionary significance are used.

Botanical classification: *Alstroemeria hybrida* 'Gina'.

Parentage:

*Female, or seed, parent.*—Proprietary selection of *Alstroemeria hybrida* identified as code number T39, not patented.

*Male or pollen parent.*—Proprietary selection of *Alstroemeria hybrida* identified as code number 1205/35, not patented.

Propagation:

*Type.*—By tissue culture.

*Root description.*—Medium in thickness; fleshy; color, close to 155C.

*Rooting habit.*—Freely branching; dense.

*Rhizome description.*—Shape: Elongate; rounded. Length: About 7 cm. Diameter: About 7 mm. Texture: Smooth. Color: Close to 155A.

Plant description:

*Plant habit.*—Compact and mounded; freely branching, bushy appearance; sturdy and strong plants; vigorous growth habit.

*Plant height.*—About 20 cm.

*Plant diameter* (*area of spread*).—About 38 cm.

Stem description:

*Aspect.*—Mostly upright to outwardly spreading.

*Internode length.*—About 0.5 cm to 3 cm.

*Strength.*—Strong, sturdy.

*Texture.*—Smooth, glabrous.

*Color.*—Close to 145D and 146B.

Foliage description:

*Arrangement.*—Alternate; below the peduncles in a single whorl; sessile.

*Length, lower leaves.*—About 8 cm.

*Length, upper leaves.*—About 5 cm.

*Width, lower leaves.*—About 2.9 cm.

*Width, upper leaves.*—About 1.5 cm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing leaves, upper surface: Close to N138A to N138B. Developing leaves, lower surface: Close to N138C. Fully expanded leaves, upper surface: Close to 137A to 137D; venation, close to 138B. Fully expanded leaves, lower surface: Close to N138D; venation, close to N138B.

Flower description:

*Flower type and habit.*—Single cup-shaped flowers arranged in compound umbels; flowers face mostly upright to outwardly; freely flowering habit; about five to ten flowers per inflorescence; about 100 flowers develop per plant.

*Natural flowering season.*—Plants begin flowering about 6 to 14 weeks after planting; in the garden, flowering is continuous from the late spring until frost in The Netherlands.

*Fragrance.*—None detected.

*Flower longevity on the plant.*—About two to three weeks on the plant; about one to two weeks as a cut flower; flowers not persistent.

*Flower buds.*—Length: About 3.9 cm. Diameter: About 1.5 cm. Shape: Ovoid. Color: Close to 144A to 144D.

*Flower diameter.*—About 5.5 cm.

*Flower depth* (*height*).—About 5.2 cm.

*Perianth.*—Arrangement: Six arranged in two whorls, each whorl with two lateral and one median segments. Size, inner perianth: Length, lateral segments: About 4.5 cm. Width, lateral segments: About 1.8 cm. Length, median segment: About 4.1 cm. Width, median segment: About 1.6 cm. Size, outer perianth: Length, lateral segments: About 4.2 cm. Width, lateral segments: About 3.1 cm. Length, median segment: About 4.5 cm. Width, median segment: About 3.4 cm. Shape, inner perianth, lateral and median segments: Lanceolate. Shape, outer perianth, lateral and median segments: Obovate. Apex, inner perianth, lateral and median segments: Acute. Apex, outer perianth, lateral and median segments: Embedded point. Base, inner perianth, lateral and median segments: Attenuate. Base, outer perianth, lateral and median segments: Cuneate. Margin, inner perianth, lateral and median segments: Entire. Margin, outer perianth, lateral and median segments: Slightly crenate. Texture, inner and outer perianths, lateral and median segments: Smooth, glabrous. Color, inner perianth: When opening, lateral segments, upper surface: Close to 9B; towards the apex, close to 60B; stripes, close to 183A. When opening, median segment, upper surface: Close to 12B; towards the apex, close to 61B; stripes, close to 183A. When opening, lateral segments, lower surface: Close to 17B; towards the apex, close to 60B; stripes, close to 177A. When opening, median segment, lower surface: Close to 58A tinted with close to 18B; stripes, close to 177A. Fully opened, lateral segments, upper surface: Close to 15A; towards the apex, close to 60A; stripes, close to 183A. Fully opened, median segment, upper surface: Close to 17C; towards the apex, close to 63A; stripes, close to 183A. Fully opened, lateral segments, lower surface: Close to 16A; towards the apex, close to 60B; stripes, close to 177A. Fully opened, median segment, lower surface: Close to 58A tinted with close to 17C; stripes, close to 177A. Color, outer perianth: When opening, lateral and median segments, upper surface: Close to 59C. When opening, lateral segments, lower surface: Close to 60B. When opening, median segment, lower surface: Close to 59C. Fully opened, lateral and median segments, upper surface: Close to 59C; with development color becoming closer to 60C. Fully opened, lateral and median segments, lower surface: Close to 59C.

*Pedicels.*—Length: About 2 cm to 6 cm. Diameter: About 2 mm. Strength: Strong. Angle: About 15° to 20° from vertical. Texture: Smooth, glabrous. Color: Close to 144A.

*Reproductive organs.*—Stamens: Quantity per flower: Five to seven. Anther shape: Oval. Anther size: About 4 mm by 7 mm. Anther color: Close to 59B. Pollen amount: Abundant. Pollen color: Close to 145C. Pistils: Quantity per flower: One. Pistil length: About 4 cm. Style length: About 3.6 cm. Style color: Close to 145C. Stigma color: Close to N57C. Ovary color: Close to 143C.

*Fruits.*—Length: About 1 cm. Diameter: About 7 mm. Color: Close to 143C.

*Seeds.*—Seed development has not been observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures ranging from about 1° C. to about 25° C.

It is claimed:

1. A new and distinct *Alstroemeria* plant named 'Gina' as illustrated and described.

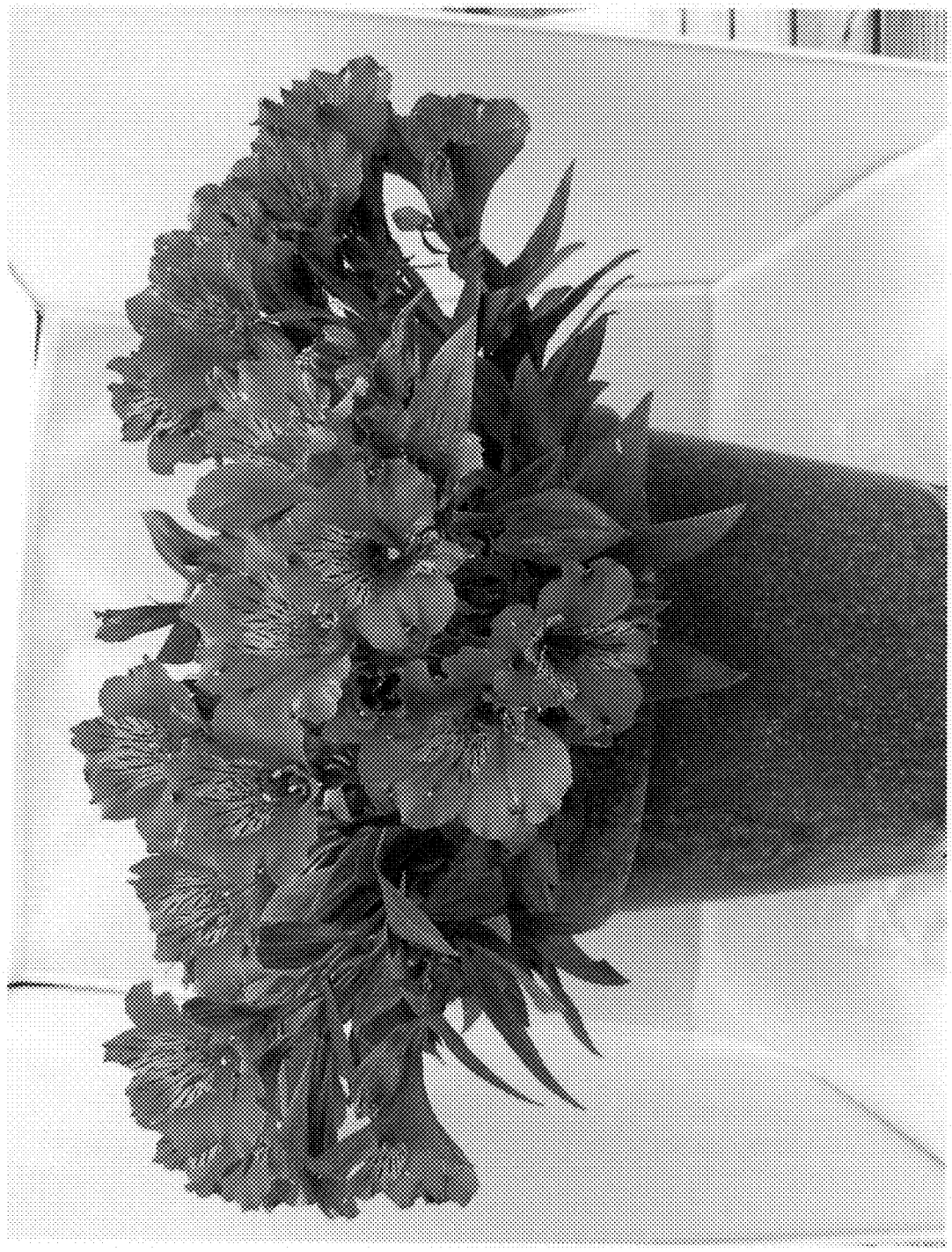

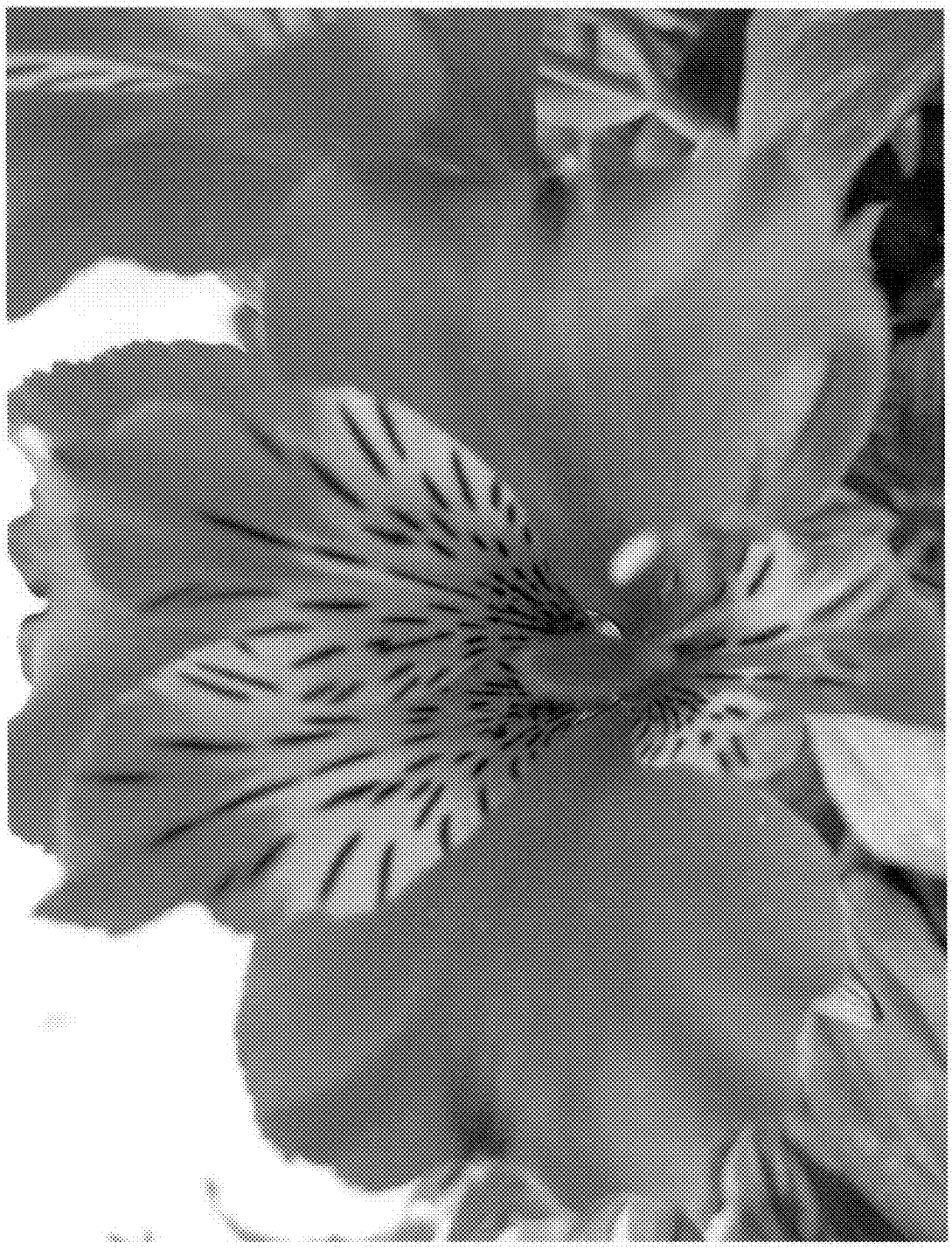

* * * * *